United States Patent [19]

Yoshinaga et al.

[11] Patent Number: 5,087,656
[45] Date of Patent: Feb. 11, 1992

[54] HIGHLY WATER-ABSORPTIVE POWDERY POLYMER COMPOSITION

[75] Inventors: Kenji Yoshinaga; Hirochika Hosaka; Toshiko Nakamura, all of Yokkaichi, Japan

[73] Assignee: Mitsubishi Petrochemical Company Limited, Tokyo, Japan

[21] Appl. No.: 491,252

[22] Filed: Mar. 9, 1990

[30] Foreign Application Priority Data

Mar. 13, 1989 [JP] Japan .................................. 1-60430

[51] Int. Cl.$^5$ .......................... C08K 3/34; C08K 7/26
[52] U.S. Cl. .................................... 524/493; 524/492; 523/220
[58] Field of Search ..................... 524/493; 523/220

[56] References Cited

U.S. PATENT DOCUMENTS

| | | | |
|---|---|---|---|
| 2,882,254 | 4/1959 | Kloepfer | 524/493 |
| 4,080,358 | 3/1978 | Krumel | 524/493 |
| 4,481,328 | 11/1984 | Harreus | 524/493 |
| 4,663,383 | 5/1987 | Lowe | 524/493 |
| 4,707,504 | 11/1987 | Walkowiak et al. | 523/220 |
| 4,732,968 | 3/1988 | Obdyashi | 524/493 |

*Primary Examiner*—Paul R. Michl
*Assistant Examiner*—Peter Szekely
*Attorney, Agent, or Firm*—Oblon, Spivak, McClelland, Maier & Neustadt

[57] ABSTRACT

A highly water-absorptive powdery polymer composition comprising a mixture of a highly water-absorptive powdery polymer and a porous powder of a high-purity silicon dioxide, said powder having (a) a mean particle size of 0.1 to 30 μm as measured by the Coulter counter method and (b) a specific surface area of 500 m$^2$/g or more as measured by the BET (Brunauer-Emmett-Teller) method.

4 Claims, 1 Drawing Sheet

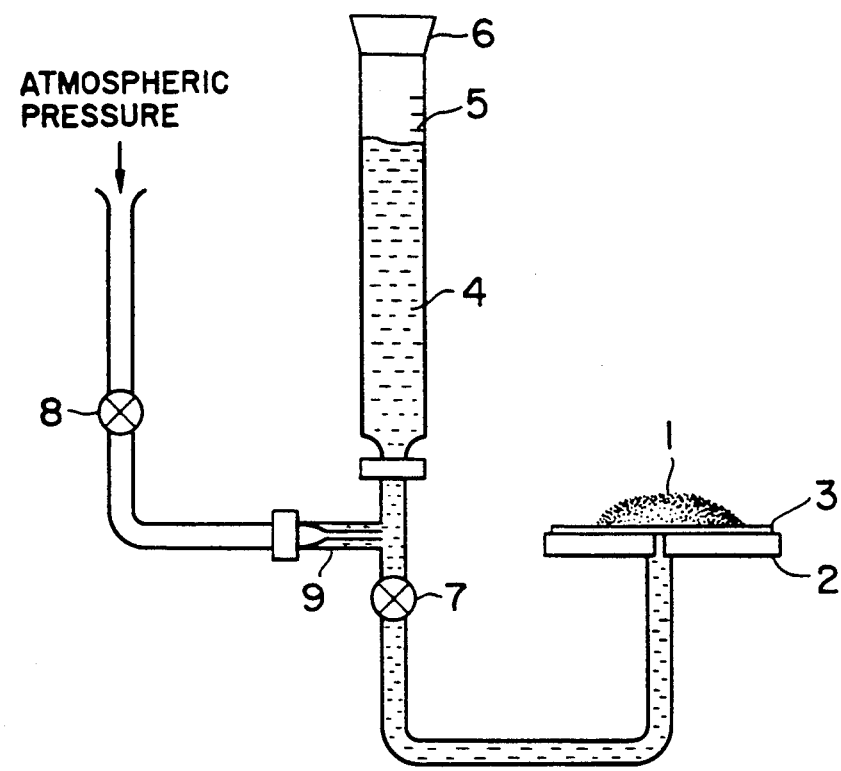
F I G. 1
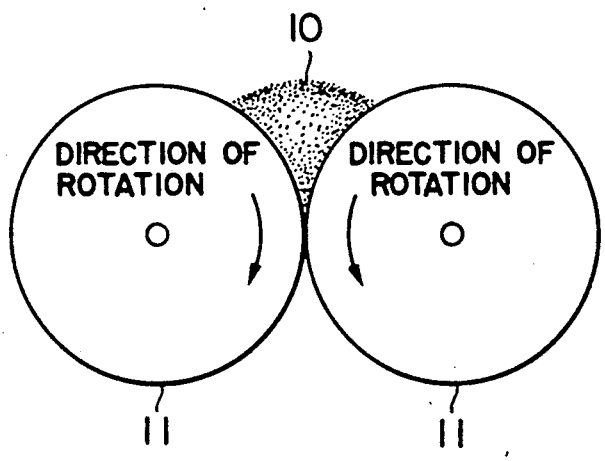
F I G. 2

## HIGHLY WATER-ABSORPTIVE POWDERY POLYMER COMPOSITION

BACKGROUND OF THE INVENTION

1. Field of the Invention

This invention relates to a highly water-absorptive powdery polymer composition.

The highly water-absorptive powdery polymer composition according to the present invention is improved in its reduced hygroscopicity and cohesiveness while maintaining various water absorption properties inherent in highly water-absorptive polymers. Particularly noteworthy is that the present powdery polymer composition is remarkably improved in its reduced adhesion to metals. Thus, it can advantageously be used for various water-absorptive materials.

2. Background Art

Highly water-absorptive polymers are synthetic polymers which have recently been used not only for sanitary goods or paper diapers in sanitary fields but also for water retentive materials, dew condensation preventive materials, freshness retentive materials and solvent dehydrating materials in industrial fields as well as in agricultural and horticultural fields, and are now expected to be applied in a wider range of fields. In general, such polymers are often processed into sheets especially when used for sanitary materials and in industrial applications. According to one process (i) applied to this end, a highly water-absorptive powdery polymer is inserted between two unwoven fabrics, which are then heat-sealed or otherwise processed into a water-absorptive sheet. According to another process (ii), cottony pulp is put on a sheet impermeable to liquid, a highly water-absorptive powdery polymer is scattered on that sheet, and cottony pulp and a sheet permeable to liquid are further placed on that sheet, followed by pressing into a water-absorptive sheet. According to a further process (iii), cottony pulp is previously mixed with a highly water-absorptive powdery polymer, and the resulting mixture is inserted between two sheets respectively permeable and impermeable to liquid, followed by pressing into a water-absorptive sheet. Other processes may also be used. In order to produce such water-absorptive sheets on an industrial scale, use is often made of machinery such as carriers, mixers, constant distributors and roll type pressing machines.

In this case, machine troubles are likely to occur due to the hygroscopicity, cohesiveness and adhesion to metals of highly water-absorptive powdery polymers. This is particularly marked when the polymers are those synthesized by reverse-phase suspension polymerization.

Various proposals have been made to decrease the hygroscopicity, cohesiveness and adhesion to metals of such highly water-absorptive powdery polymers. For instance, there have been proposed:

(a) granulation of powder into granules,
(b) removal of fine powder by classification,
(c) surface treatment for coating a hydrophobic substance on the surface of polymers,
(d) mixing of polymers with specific hydrophobic ultrafine silica particles, as disclosed in Japanese Patent Kokai Publication No. 133028/1981.

So far as the present inventors know, however, the above method (a) needs complicated steps, and the method (b) is disadvantageous in the light of production yield. A problem with the method (c) is that the water absorption capacity of the polymer treated is excessively reduced. With the method (d), it is not easy to effect uniform mixing of polymers with such ultrafine particles. Taken altogether, the above methods (a) to (d) have some effects upon reduction in the hygroscopicity and cohesiveness of highly water-absorptive powdery polymers. However, they are little effective for reduction in the adhesion to metals of highly water-absorptive powdery polymers, especially with polymers prepared by reverse-phase suspension polymerization.

In other words, the hygroscopicity, cohesiveness and adhesion to metals of highly water-absorptive powdery polymers prepared by, esp., reverse-phase suspension polymerization are not simultaneously improved to satisfactory levels. In this regard, there is left much to be desired.

SUMMARY OF THE INVENTION

The present invention is intended to provide a highly water-absorptive powdery polymer composition which is simultaneously improved in terms of hygroscopicity, cohesiveness and adhesion to metals without causing damage to the water absorption properties inherent in a highly water-absorptive powdery polymer.

As a result of various studies made so as to solve the aforesaid problems, the present inventors have found that a highly water-absorptive powdery polymer composition, which may be prepared by mixing and dispersing a porous fine powder of high-purity silicon dioxide having a large internal surface area with and in a highly water-absorptive polymer, successfully achieves the object and provides a solution to the aforesaid problems. The present invention has been accomplished based on such finding.

Thus, the highly water-absorptive powdery polymer composition according to the present invention comprises a mixture of a highly water-absorptive powdery polymer and a porous powder of a high-purity silicon dioxide, said powder having (a) a mean particle size of 0.1 to 30 μm as measured by the Coulter counter method and (b) a specific surface area of 500 m$^2$/g or more as measured by the BET (Brunauer-Emmett-Teller)method.

BRIEF DESCRIPTION OF THE DRAWINGS

FIG. 1 is a schematic view illustrative of a device used to measure the rate of water absorption and water retention capacity of a highly water-absorptive powdery polymer (composition), and FIG. 2 is a schematic view illustrative of a device used to determine the adhesion-to-metals of a highly water-absorptive powdery polymer (composition).

Throughout the drawings, reference numeral 1 stands for a highly water-absorptive polymer (composition) (1 g), 2 a support board with a small hole, 3 an unwoven fabric, 4 0.9% saline solution, 5 a burette, 6 a rubber plug, 7 & 8 valves, 9 an air inlet, 10 a highly water-absorptive polymer (composition) and 11 a roller.

DETAILED DESCRIPTION OF THE INVENTION

Highly Water-Absorptive Polymer

The highly water-absorptive powdery polymer used in the present invention, with and in which the fine powder of high-purity silicon dioxide is to be mixed and dispersed, may be selected from the group consisting of a hydrolyzate of starch/acrylonitrile graft copolymer, a crosslinked product of carboxymethylcellulose, a crosslinked product of polyacrylic acid (or its salt), a copolymer of acrylic acid (or its salt) and vinyl alcohol, a crosslinked product of polyethylene oxide and so on.

Preferably, the highly water-absorptive polymer powder has a mean particle size of 10 to 2000 μm, esp., 50 to 1000 μm.

Such highly water-absorptive polymers may be those obtained by known conventional methods or commercially available products. Especially remarkable effects are obtained when using polymers prepared by the reverse-phase suspension polymerization of an acrylic monomer selected from the group consisting of acrylic acid, methacrylic acid, and their alkali metal salts in a hydrocarbon solvent containing a surfactant with the use of a radical polymerization initiator.

Given below are details of the highly water-absorptive polymers synthesized from such acrylic monomers.

It is to be understood that the present invention is not limited to such preferable highly water-absorptive polymers as mentioned below and, hence, to those obtained with the use of a radical polymerization initiator and/or a surfactant.

Acrylic Monomer

The highly water-absorptive powdery polymer particularly preferable for constituting the highly water-absorptive polymer composition according to the present invention is one produced from an acrylic monomer selected from the group consisting of acrylic acid and/or methacrylic acid and their alkali metal salts. It is here to be noted that the "alkali metal salts" refer to salts obtained by the neutralization of the carboxyl groups of acrylic acid and/or methacrylic acid with an alkali metal hydroxide such as sodium hydroxide, potassium hydroxide or lithium hydroxide. In view of the quality, price, etc. of the resulting polymers, particular preference is given to a salt obtained by the neutralization of acrylic acid and/or methacrylic acid with sodium hydroxide.

It is also to be noted that the "highly water-absorptive powdery polymer produced from an acrylic monomer selected from the group consisting of acrylic acid and/or methacrylic acid and their alkali metal salts" does not exclude the presence of other components that do not hinder the achievement of the object of the present invention or other monomers or components that favor the present invention.

When taking into account the properties of the highly water-absorptive polymer, the degree of neutralization of acrylic acid and/or methacrylic acid is one of very important factors. In order to make the properties of the resulting highly water-absorptive polymer well-balanced, it is desired that 50 to 95 mol % of the entire carboxyl groups in the acrylic monomers are neutralized. If the degree of neutralization is below 50 mol %, there can then be a drop of water absorption capacity, which makes it difficult to keep the properties of polymers well-balanced. When the degree of neutralization is more than 95 mol %, on the other hand, the rate of polymerization is too slow.

The concentration of such acrylic monomers in a solution is preferably in a range of 20% to 70%, more preferably 30% to 60% inclusive.

In the present invention, the aforesaid acrylic monomers may be used in combination with other monomers copolymerizable therewith such as, for instance, maleic acid (salt), itaconic acid (salt), acrylamide, 2-acrylamide-2-methylpropane sulfonate , 2-(meth)acryloylethane sulfonate and 2-hydroxyethyl (meth)acrylate, provided that they cause no substantial damage to the water absorption properties of the water-absorptive polymers.

Radical Polymerization Initiator

When the above mentioned acrylic monomers are polymerized by reverse-phase suspension polymerization into highly water-absorptive polymers, it is usual to previously dissolve a water-soluble radical polymerization initiator in an aqueous monomer solution. As the water-soluble polymerization initiator, use may typically be made of a persulfate such as potassium persulfate or ammonium persulfate, or an azo initiator such as azobis-(2-amidinopropane) dihydrochloride. These radical polymerization initiators are usually used in an amount of about 0.001 to 5% by weight, preferably about 0.01 to 1.0% by weight based on the amount of an aqueous monomer solution.

Hydrocarbon Solvent

The solvents to be preferably used for reverse-phase suspension polymerization are aliphatic or alicyclic hydrocarbons. Examples of such solvents include n-pentane, n-hexane, n-heptane, cyclohexane and ligroin. Among these, cyclohexane and n-hexane are particularly preferred in view of the removal of polymerization heat and the drying of polymers.

Surfactant

Surfactants may be used arbitrarily, according to necessity, for the purpose of stabilizing an aqueous monomer solution in a hydrocarbon solvent in the form of waterdrops, and have a considerable influence upon the particle size and apparent flowability of polymer product. To this end, various surfactants have been proposed. Preferred surfactants to be used in the present invention may include sorbitan fatty acid esters represented by sorbitan monostearate or sorbitan monolaurate, glycerin fatty acid esters such as glycerin monostearate, a polyglycerin fatty acid ester, a polyoxyethylene sorbitan fatty acid ester, a polyoxyethylene alkyl ether, a cellulosic protective colloid, a sucrose fatty acid ester and so on. These surfactants may suitably be used at a concentration of 0.1 to 10% by weight, preferably 0.5 to 5% by weight in a hydrocarbon solvent.

Polymerization

The order and manner of addition of the above mentioned acrylic monomers, radical polymerization initiators and surfactants as well as the operating procedures of polymerization are not particularly limited in carrying out polymerization to produce the highly water-absorptive powdery polymer according to the invention. Polymerization may be carried out, for example, in a manner such that (a) an aqueous solution of an acrylic monomer, in which a crosslinking agent and a radical polymerization initiator have been dissolved, is added to and suspended in a hydrocarbon solvent containing a surfactant, followed by heating to carry out polymerization; (b) a surfactant is added to an aqueous solution of an acrylic monomer in which a crosslinking agent and a radical polymerization initiator have been dissolved, and the resulting solution is then added to and suspended in a hydrocarbon solvent, followed by heating to carry out polymerization; (c) an aqueous solution of an acrylic monomer, in which a crosslinking agent and a radical polymerization initiator have been dissolved, is added to and suspended in a hydrocarbon solvent, and a surfactant is then added to the resulting solution, followed by heating to carry out polymerization; and so on.

The polymerization temperature used is generally in a range of 40° to 120° C., preferably 60° to 90° C. Although varying with the polymerization temperature, etc., the polymerization time is generally in a range of about 30 minutes to 6 hours, preferably about 1 to 4 hours.

High-Purity Silicon Dioxide

The high-purity silicon dioxide to be used in the present invention should be in the form of porous fine powder having a large internal surface area.

More specifically, use should be made of high-purity silicon dioxide powder having (a) a mean particle size of 0.1 to 30 $\mu$m, preferably 0.3 to 20 $\mu$m, more preferably 1 to 10 $\mu$m as measured by the Coulter counter method and (b) a specific surface area of 500 $m^2/g$ or more as measured by the BET (Brunauer-Emmett-Teller) method. When the mean particle size and specific surface area fall out of the aforesaid ranges, it is then required to increase the amount of the silicon dioxide added in order to achieve the intended effect of the present invention, thus offering disadvantages in view of economical consideration and difficulty in its good dispersion.

The term "high-purity" used herein with respect to silicon dioxide refers to a pure silicon dioxide content of at least 99.5%. Referring to the amount of the high-purity silicon dioxide mixed with and dispersed in the highly water-absorptive powdery polymer, while it varies depending upon how much improvements are to be achieved, it is used generally in an amount of 0.001 to 10 parts by weight, preferably 0.005 to 5 parts by weight per 100 parts by weight of the highly water-absorptive powdery polymer so as to achieve a satisfactory improvement simultaneously in hygroscopicity, cohesiveness and adhesion to metals. In some cases, the silicon dioxide may be added in an amount exceeding the above upper limit. In that case, however, care should be taken of some possible problems arising in connection with the properties of compositions for use in certain applications.

Composition

The composition according to the present invention may be obtained, for example, by uniformly mixing and dispersing the predetermined amount of the above specific silicon dioxide with and in the above preferable highly water-absorptive powdery polymer. Although mixing and dispersion may be carried out by a number of known conventional manners or means, they are easily achievable with a mixer generally used for powder mixing.

The thus obtained composition of the present invention is simultaneously improved in terms of hygroscopicity, cohesiveness and adhesion to metals with no deterioration of the water absorption properties inherent in the highly water-absorptive powdery polymer, and are thus applicable to various fields.

Experimental Examples

The present invention will now be explained in detail with reference to the following experimental examples. In the examples, the water absorption properties of the high water-absorptive powdery polymer composition were determined in terms of the water absorption capacity and rate of water absorption (diffusion), which were measured according to the method indicated below. Also given below are methods for measuring the hygroscopicity, cohesiveness and adhesion to metals of the highly water-absorptive powdery polymer composition.

Water Absorption Capacity 1.0 g of a sample of a highly water-absorptive polymer composition was placed in a 400-mesh nylon bag (of 10 cm $\times$ 10 cm), which was immersed in 0.9% saline solution for 30 minutes. After 30 minutes, the nylon bag was pulled up and drained off for 15 minutes and then its weight was measured. Based on the weight difference from the weight of the nylon bag housing a blank sample, the water absorption capacity was determined as the weight of 0.9% saline solution absorbed in 1 g of the composition.

Rate of Water Absorption (Diffusion)

Measurement was carried out using the device shown in FIG. 1. 1.0 g of a sample of a highly water-absorptive polymer composition was placed on an unwoven fabric on a support board with a small hole. The amount of 0.9% saline solution absorbed by the sample upon contact thereof with the solution was measured. The rate of water absorption (diffusion) was determined as the amount of 0.9% saline solution absorbed after 10 minutes of initiation.

Hygroscopicity & Cohesiveness 50 g of a highly water-absorptive powdery polymer composition was uniformly placed on a petri dish of 15 cm in diameter, which was then put in a thermo-hygrostat maintained at a temperature of 25° C. and a relative humidity of 80%. Two hours later, weight gains and state changes were observed to evaluate how hygroscopicity and cohesiveness were improved.

Adhesion to Metals

A sample of polymer composition was placed on the upper portions of two rollers (SUS304) fixed by a shaft of 5 cm in diameter and 30 cm in length, which were then rotated and the adhesion of the sample to the rollers was examined visually.

FIG. 2 indicates a schematic view of the device used for this test.

HIGHLY WATER-ABSORPTIVE POLYMER

The highly water-absorptive powdery polymers herein tested were synthesized as follows.

Highly Water-Absorptive Polymer (A)

In a four-necked round flask of 5000 ml in volume provided with a stirrer, a reflux cooler, a thermometer and a nitrogen gas supply tube, was placed 1210 g of cyclohexane, to which was added and dissolved therein 9 g of sorbitan monostearate. Afterwards, dissolved oxygen was expelled by blowing a nitrogen gas into the flask.

Separately, 122.6 g of sodium hydroxide with 95% purity dissolved in 796.5 g of water was added to 300 g of acrylic acid in a beaker of 2000 ml in volume, while externally cooling with ice, thereby neutralizing 70% of the carboxyl groups. In this case, the concentration of the monomer in water corresponds to 30%, as measured for the neutralized monomer. Then, to this solution were added and dissolved therein 0.42 g of N,N'-methylenebisacrylamide and 1.04 g of potassium persulfate. Thereafter, dissolved oxygen was expelled by blowing a nitrogen gas into the solution.

Next, the content of the above beaker was added to the content of the above four-necked round flask, followed by mixing under agitation. Then, the internal (Sunwet IM-1000®, manufactured by Sanyo Kasei Co., Ltd.).

Fine powder of high-purity silicon dioxide was added to and uniformly mixed with the highly water-absorptive powdery polymer (A) or (B).

The types and amounts of the highly water-absorptive powdery polymers and high-purity silicon dioxides used were shown in Table 1.

TABLE 1

|  | Polymers and their Amount | High-Purity Silicon Dioxide | | Amount |
| --- | --- | --- | --- | --- |
| Ex. 1 | Polymer (A) 100 g | Trade Name: Syloid 63 Fuji-Davison Chemical Co., Ltd. | Mean particle size: 6.0μ Specific surface area: 700 m²/g | 0.01 g |
| Ex. 2 | Polymer (A) 100 g | Trade Name: Syloid 63 Fuji-Davison Chemical Co., Ltd. | Mean particle size: 6.0μ Specific surface area: 700 m²/g | 0.05 g |
| Ex. 3 | Polymer (A) 100 g | Trade Name: Syloid 63 Fuji-Davison Chemical Co., Ltd. | Mean particle size: 6.0μ Specific surface area: 700 m²/g | 0.5 g |
| Ex. 4 | Polymer (A) 100 g | Trade Name: Syloid 63 Fuji-Davison Chemical Co., Ltd. | Mean particle size: 6.0μ Specific surface area: 700 m²/g | 2.0 g |
| Ex. 5 | Polymer (A) 100 g | Trade Name: Syloid 66 Fuji-Davison Chemical Co., Ltd. | Mean particle size: 3.0μ Specific surface area: 700 m²/g | 0.5 g |
| Ex. 6 | Polymer (A) 100 g | Trade Name: Syloid 66 Fuji-Davison Chemical Co., Ltd. | Mean particle size: 3.0μ Specific surface area: 700 m²/g | 2.0 g |
| Ex. 7 | Polymer (B) 100 g | Trade Name: Syloid 63 Fuji-Davison Chemical Co., Ltd. | Mean particle size: 6.0μ Specific surface area: 700 m²/g | 0.1 g |
| Ex. 8 | Polymer (B) 100 g | Trade Name: Syloid 63 Fuji-Davison Chemical Co., Ltd. | Mean particle size: 6.0μ Specific surface area: 700 m²/g | 0.5 g |
| Ex. 9 | Polymer (B) 100 g | Trade Name: Syloid 63 Fuji-Davison Chemical Co., Ltd. | Mean particle size: 6.0μ Specific surface area: 700 m²/g | 2.0 g | temperature of the flask was increased in an oil bath while bubbling a nitrogen gas. As a result, the internal temperature reached around 60° C., then rose rapidly and finally reached 75° C. after tens of minutes. While that internal temperature was maintained at 60° to 65° C., reaction was carried out for 3 hours with stirring at 145 rpm. When stirring was stopped, wet polymer particles settled down on the bottom of the round flask. These particles could easily be separated from the cyclohexane phase by decantation.

The separated wet polymer was transferred into a vacuum dryer, where it was heated to 90° C. to remove cyclohexane and water attached to the polymer. As a result, 400 g of highly water-absorptive dry polymer powder was obtained.

Comparative Examples 1 & 2

Measurements were made of the water absorption capacity, rate of water absorption (diffusion), hygroscopicity, cohesiveness and adhesion to metals of the highly water-absorptive powdery polymer (A) and (B) with which no high-purity silicon dioxide was mixed.

Comparative Examples 3 to 9

Fine powders of various types of high-purity silicon dioxide were added to and uniformly mixed with the highly water-absorptive powdery polymers.

The types and amounts of the highly water-absorptive polymers and high-purity silicon dioxides used were shown in Table 2.

TABLE 2

|  | Polymers and their Amount | High-Purity Silicon Dioxide | | Amount |
| --- | --- | --- | --- | --- |
| Comp. Ex. 1 | Polymer (A) 100 g | — | — | — |
| Comp. Ex. 2 | Polymer (B) 100 g | — | — | — |
| Comp. Ex. 3 | Polymer (A) 100 g | Trade Name: Aerosil 130 (Japan Aerosil Co., Ltd.) | Mean particle size: 0.016μ Specific surface area: 130 m²/g | 0.5 g |
| Comp. Ex. 4 | Polymer (A) 100 g | Trade Name: Aerosil 200 (Japan Aerosil Co., Ltd.) | Mean particle size: 0.012μ Specific surface area: 200 m²/g | 0.5 g |
| Comp. Ex. 5 | Polymer (A) 100 g | Trade Name: Aerosil R-972 (Japan Aerosil Co., Ltd.) | Mean particle size: 0.016μ Specific surface area: 110 m²/g | 0.5 g |
| Comp. Ex. 6 | Polymer (A) 100 g | Trade Name: Syloid 244 (Fuji-Davison Chemical Co., Ltd.) | Mean particle size: 1.8μ Specific surface area: 300 m²/g | 1.0 g |
| Comp. Ex. 7 | Polymer (A) 100 g | Trade Name: Microbead MB-3A (Fuji-Davison Chemical Co., Ltd.) | Mean particle size: 40μ Specific surface area: 650 m²/g | 5.0 g |
| Comp. Ex. 8 | Polymer (B) 100 g | Trade Name: Aerosil 130 (Japan Aerosil Co., Ltd.) | Mean particle size: 0.016μ Specific surface area: 130 m²/g | 0.5 g |
| Comp. Ex. 9 | Polymer (B) 100 g | Trade Name: Syloid 244 (Fuji-Davison Chemical Co., Ltd.) | Mean particle size: 1.8μ Specific surface area: 300 m²/g | 1.0 g |

Highly Water-Absorptive Polymer (B)

For this polymer, use was made of a crosslinked product of starch/acrylic acid (salt) graft copolymer The following is a description of the tradename items mentioned in the examples above.

Sunwet IM-1000: A white, powdered crosslinked starch/acrylic acid (salt) graft copolymer having a deionized water absorptive capacity of 1000 g per gram of polymer, a physiological salt solution absorptive capacity of 80 g per gram of polymer, a 1.6% salt solution absorptive capacity of 65 g per 1 g of polymer and a stock blood (sheep blood) absorptive capacity of 80 g per 1 g of polymer; a pH of neutral of a 0.1% solution of the polymer in water; an apparent density of 0.4 g/ml; a water content of 7 wt. % or less, a particle size distribution of 1 wt. % of 20 mesh or larger, 89 wt. % of particles ranging from 20 to 145 mesh, and 10 wt. % of 145 mesh or smaller.

| SYLOID | Ave. Particle Size (μ) by Coulter Counter | Loss on Ignition (%) at 950° C. | pH (5% slurry) | Color (Hunter) | Surface Area (m²/g) by BET Method | Oil Adsorption (ml/100 gr) (JIS K5101 1 g) | Net (kg) | Packing Style (standard) |
|---|---|---|---|---|---|---|---|---|
| 63 | 5.0 | 11.0 | 4.0 | 90 | 700 | 90 | 8 | Can (18 l) |
| 66 | 2.5 | 11.0 | 4.0 | 90 | 700 | 90 | 20 | Paper Bag |
| 244 | 2.0 | 5.0 | 7.5 | 94 | 300 | 310 | 10 | Poly Ethylene Bag |

| Test method | DIM | AEROSIL 130 | AEROSIL 200 | AEROSIL R972 |
|---|---|---|---|---|
| Behavior towards water | | | | |
| Appearance | | | | |
| BET surface area[1] | m²/g | 130 ± 25 | 200 ± 25 | 110 ± 20 |
| Average primary particle size | Nanometer | 16 | 12 | 16 |
| Tamped density[2] | | | | |
| Standard material | g/l | appr. 50 | appr. 50 | appr. 50 |
| Densed material (add "V") | g/l | appr. 120 | appr. 120 | appr. 90 |
| Moisture[3] when leaving plant site (2 hours at 105° C.) | % | <1.5 | <1.5 | <0.5 |
| Ignition loss[4][7] (2 hours at 1000° C.) | % | <1 | <1 | <2[12] |
| pH[5] (in 4% aqueous dispersion) | | 3.6–4.3 | 3.6–4.3 | 3.6–4.3[10] |
| $SiO_2$[8] | % | >99.8 | >99.8 | >99.8 |
| $Al_2O_3$[8] | % | <0.05 | <0.05 | <0.05 |
| $Fe_2O_3$[8] | % | <0.003 | <0.003 | <0.01 |
| $TiO_2$[8] | % | <0.03 | <0.03 | <0.03 |
| $HCl$[5][11] | % | <0.025 | <0.025 | <0.05 |
| Sieve residue[8] (by Mocker, 45 μm) | % | <0.05 | <0.05 | — |

[1] acc. to DIN 66 131
[2] acc. to DIN ISO 787/XI, JIS K 5101/18
[3] acc. DIN ISO 787/II, ASTM D 260, JIS K 5101/21
[4] acc. to DIN 55 921, ASTM D 1208, JIS K 5101/23
[5] acc. to DIN ISO 797/IX, ASTM O 1208, JIS K 5101/24
[6] acc. to DIN ISO 787/XVIII, JIS K 5101/20
[7] dried for 2 hours at 105° C.
[8] ignited for 2 hours at 1000° C.
[9] special moisture-protective packaging
[10] in water acetone or methanol ≈ 1:1
[11] HCl-content is a part of ignition loss
[12] contains approx. 1% chemically bonded carbon
[13] contains approx. 5% chemically bonded carbon
[14] contains approx. 7% chemically bonded carbon
[15] contains approx. 3.5% chemically bonded carbon Microbead MB-3A has a surface area of 650 m²/g, an average pore diameter of 2.5 nm, a pore volume of 0.40 ml/g, a packing density of 0.7 g/ml, a pH of 4.0 (5% slurry) and a particle size distribution of 30 μm–200 mesh, 100 μm–200 mesh.

Table 3 shows the results of the water absorption capacity, rate of water absorption (diffusion), hygroscopicity, cohesiveness and adhesion to metals of the highly water-absorptive powdery polymer compositions set forth in Tables 1 and 2.

The mean particle sizes of the high-purity silicon dioxides shown in Tables 1 and 2 were all measured by the Coulter counter method, while the specific surface areas thereof were all determined by the BET method.

TABLE 3

| | Water Absorption Capacity (g/g polymer) | Rate of Water Absorption (g/g polymer) | Hygroscopicity, Cohesiveness | | Adhesion to Metals |
|---|---|---|---|---|---|
| | | | Weight gains (g) | State changes | |
| Ex. 1 | 65 | 50 | 1.9 | No change | No adhesion |
| Ex. 2 | 67 | 50 | 1.2 | No change | No adhesion |
| Ex. 3 | 64 | 48 | 1.5 | No change | No adhesion |
| Ex. 4 | 59 | 44 | 1.4 | No change | No adhesion |
| Ex. 5 | 66 | 51 | 1.0 | No change | No adhesion |
| Ex. 6 | 63 | 50 | 1.0 | No change | No adhesion |
| Ex. 7 | 40 | 17 | 2.4 | No change | No adhesion |
| Ex. 8 | 41 | 16 | 2.5 | No change | No adhesion |
| Ex. 9 | 39 | 14 | 2.0 | No change | No adhesion |
| Comp. Ex. 1 | 65 | 50 | 2.9 | Surface film | Much adhesion |
| Comp. Ex. 2 | 40 | 17 | 4.3 | Solidification | some adhesion |
| Comp. Ex. 3 | 65 | 51 | 2.5 | Cohesion | some adhesion |
| Comp. Ex. 4 | 63 | 49 | 2.6 | Cohesion | some adhesion |
| Comp. Ex. 5 | 62 | 46 | 4.0 | No change | some adhesion |
| Comp. Ex. 6 | 64 | 46 | 1.4 | Cohesion | some adhesion |
| Comp. Ex. 7 | 60 | 21 | 4.2 | Solidification | Much adhesion |
| Comp. Ex. 8 | 38 | 15 | 3.9 | Cohesion | No adhesion |
| Comp. Ex. 9 | 38 | 16 | 3.6 | Cohesion | No adhesion |

From the results shown in Table 3, it is apparent that the highly water-absorptive powdery polymer compositions according to the present invention are simultaneously improved in terms of their hygroscopicity, state after moisture absorption and adhesion to metals without causing damage to the water absorption properties inherent in the highly water-absorptive polymers.

We claim:

1. A water-absorptive powdered polymer composition comprising a mixture of a water-absorptive polymer produced from an acrylic monomer selected from the group consisting of acrylic acid, methacrylic acid and their alkali metal salts and a porous powder of a silicon dioxide, said powder having (a) a mean particle size of 0.1 to 30 $\mu$m, a measured by the Coulter counter method, and (b) a specific surface area of 500 $m^2/g$ or more as measured by the BET (Brunauer-Emmett-Teller) method.

2. The composition according to claim 1, wherein the acrylic monomer is an alkali metal salt of acrylic acid and/or methacrylic acid.

3. The composition according to claim 2, wherein the alkali metal salt is sodium salt.

4. The composition according to claim 2 or 3, wherein the alkali metal salt has a neutralization degree of 50 to 95 mol %.

* * * * *